United States Patent [19]

Burton et al.

[11] 4,439,374

[45] Mar. 27, 1984

[54] PROCESS FOR SULFONATING IMPURE ORTHO ALKYLPHENOL

[75] Inventors: Lester P. J. Burton, Pleasant Ridge; Ronald L. Shubkin, West Bloomfield, both of Mich.

[73] Assignee: Ethyl Corporation, Richmond, Va.

[21] Appl. No.: 392,656

[22] Filed: Jun. 28, 1982

[51] Int. Cl.$^3$ ..................... C07C 143/44; C07C 79/28
[52] U.S. Cl. ................................ 260/512 R; 568/703; 568/711
[58] Field of Search .................... 260/512 R; 568/711, 568/703

[56] References Cited

U.S. PATENT DOCUMENTS

| | | | |
|---|---|---|---|
| 2,048,168 | 7/1936 | Pollard | 568/711 |
| 2,192,197 | 3/1940 | Mills et al. | 568/711 |
| 2,256,195 | 9/1941 | Filbert | 568/711 |
| 2,392,859 | 1/1946 | Meuli | 71/122 |
| 2,672,485 | 3/1954 | Menn et al. | 568/703 |
| 2,810,767 | 10/1957 | Clarke et al. | 568/711 |
| 3,752,858 | 8/1973 | Odenweller | 568/711 |
| 3,766,254 | 10/1973 | Sharman et al. | 260/512 R |
| 3,829,470 | 8/1974 | Hannah | 260/512 R |

*Primary Examiner*—Nicky Chan
*Attorney, Agent, or Firm*—Donald L. Johnson; John F. Sieberth; Joseph D. Odenweller

[57] ABSTRACT

The sulfonation of o-alkylphenols by reaction with sulfuric acid is improved to give higher conversion to disulfonated o-alkylphenol by adding a small amount of a polybasic carboxylic acid (e.g. oxalic acid) to the o-alkylphenol. The sulfonated product is converted to a dinitro-o-alkylphenol by reaction with nitric acid or salt thereof.

11 Claims, No Drawings

PROCESS FOR SULFONATING IMPURE ORTHO ALKYLPHENOL

BACKGROUND

Dinitro-o-sec-butylphenol is a commercial herbicide. It can be made by reacting o-sec-butylphenol with concentrated sulfuric acid to form a sulfonated o-sec-butylphenol which can be reacted with aqueous sodium nitrate to form mainly 2,4-dinitro-6-sec-alkylphenol. This reaction sequence as applied to higher alkylphenols is described in U.S. Pat. No. 2,810,767. It is also known to use nitric acid in place of the aqueous sodium nitrate as the nitrating agent.

Although the above reaction sequence works well with highly purified colorless o-sec-butylphenol, it is not completely satisfactory with less pure o-sec-butylphenol which is slightly yellow to amber in color. With such impure o-sec-butylphenol starting material, the conversion to disulfonated o-sec-alkylphenol is incomplete, and the final product after the nitration is dark in color and contains a tar-like residue. Thus, a need exists to render impure o-sec-butylphenol satisfactory for sulfonation and nitration without an extensive purification procedure.

SUMMARY

It has now been discovered that impure discolored o-sec-butylphenol can be successfully sulfonated by reaction with concentrated sulfuric acid to form a product high in disulfonate content which converts readily to 2,4-dinitro-6-sec-butylphenol of high quality.

DESCRIPTION OF THE PREFERRED EMBODIMENTS

A preferred embodiment of the invention is an improvement in the process of sulfonating an impure ortho-alkylphenol to form a disulfonated o-alkylphenol, said process comprising reacting an o-alkylphenol with concentrated sulfuric acid. According to the present improvement, a small amount of a polybasic carboxylic acid or salt thereof is added to impure o-alkylphenol. The improvement results in a reaction product having an increased ratio of disulfonated-o-alkylphenol to monosulfonated o-alkylphenol.

The main use of the sulfonated o-alkylphenol is as a starting material for conversion to dinitro-o-alkylphenol. These compounds are herbicides as disclosed in U.S. Pat. No. 2,392,859. Accordingly, a further embodiment of the invention is a process for making 2,4-dinitro-6-alkylphenol, said process comprising (a) mixing about 0.0001–0.5 weight percent of a polybasic carboxylic acid or salt thereof with an o-alkylphenol, (b) reacting said o-alkylphenol containing said polybasic carboxylic acid or salt with concentrated sulfuric acid in an amount of at least 2.0 moles of sulfuric acid per mole of said o-alkylphenol at a temperature of about 30°–150° C. to form sulfonated o-alkylphenol, (c) reacting said sulfonated o-alkylphenol with a nitrating agent selected from the group consisting of nitric acid, and salts thereof in an amount of at least 2.0 moles of nitrating agent per mole of said o-alkylphenol at a temperature of about 30°–150° C. and (d) recovering a dinitro-o-alkylphenol product of high purity being substantially free of insoluble tar.

A broad range of o-alkylphenol can be used in the process. The alkyl group can be primary, secondary or tertiary. Preferably, the alkyl is primary or secondary because tertiary alkyl groups are susceptible to dealkylation in the process. The alkyl groups can contain from 1–20 or more carbon atoms. Examples of these are o-cresol, o-ethylphenol, o-isopropylphenol, o-(n-hexyl)-phenol, o-(n-octyl)phenol, o-(n-octadecyl)phenol, o-(n-eicosyl)phenol, o-(1-methylundecyl)phenol, o-sec-amylphenol, o-sec-octylphenol, o-sec-dodecylphenol, o-sec-eicosylphenol, and the like.

More preferably, the o-alkyl group is a sec-alkyl containing about 3–12 carbon atoms. These include o-isopropylphenol, o-sec-butylphenol, o-(1-methylpentyl)-phenol, o-(1-methylheptyl)phenol, o-(1-methylundecyl)phenol, o-(1-ethylbutyl)phenol, and the like.

The most important o-alkylphenol is o-sec-butylphenol because of its usefulness in making dinitro-o-sec-butylphenol.

Polybasic carboxylic acids have been described as color and odor stabilizers for alkylphenols. This use is described in U.S. Pat. No. 2,672,485. They are said to prevent color and odor formation in alkylphenols on aging.

Polybasic carboxylic acids that can be used in the present process include those aliphatic carboxylic acids having 2 or more carboxylic acid groups. Preferably, the acid contains 2 or 3 carboxylic acid groups and 2–12 carbon atoms. Representative examples include oxalic, malonic, succinic, glutaric, adipic, pimelic, suberic, azelaic, sebacic, and the like, including mixtures thereof and salts thereof.

More preferably the carboxylic acids are oxalic, citric, or tartaric including mixtures and salts thereof.

Salts of the carboxylic acids can be used. In the concentrated sulfuric acid system, these are converted to acid. Such salts include alkali metal salts (e.g. sodium, potassium, and the like), alkaline earth metal salts, (e.g. calcium, barium, magnesium, and the like) and ammonium salts.

The most preferred polycarboxylic acid is oxalic acid.

The polybasic acid should be present during the reaction of the o-alkylphenol with the sulfuric acid. This can be accomplished by adding the sulfuric acid, o-alkylphenol and polybasic acid separately to a reaction vessel. Alternatively, the polybasic acid could be mixed with the sulfuric acid and this mixture reacted with the o-alkylphenol. Preferably, the polybasic acid is first mixed with the o-alkylphenol, and this mixture reacted with the sulfuric acid.

Only a small amount of the polybasic acid is required. The optimum amount can readily be determined in a few experiments. A useful range is about 0.0005–1.0 weight percent. A more preferred range is about 0.001–0.5 weight percent.

The sulfonation temperature should be high enough to cause the sulfonation to proceed but not so high as to cause excessive decomposition of the reactants or products. A useful temperature range in which to experiment is about 20°–200° C. A more preferred temperature range is about 30°–150° C. Excellent results have been achieved with o-sec-butylphenol at about 70°–95° C.

Concentrated sulfuric acid is used in the sulfonation. Preferably, the sulfuric acid is at least 90 weight percent $H_2SO_4$ and more preferably at least 95 weight percent $H_2SO_4$. Optionally, oleum may be used in the sulfonation. Oleum can contain up to about 30 percent or more sulfur trioxide.

The amount of sulfuric acid should be sufficient to provide at least about 2 moles of $H_2SO_4$ per mole of o-alkylphenol because disulfonation is the goal of the reaction. A useful range is about 2-5 moles of sulfuric acid per mole of o-alkylphenol. A more preferable range is about 2.5-3.5 moles of sulfuric acid per mole of o-alkylphenol. Good results have been achieved using about 2.3 moles of sulfuric acid per mole of o-sec-butylphenol.

The sulfonation time is not critical. This depends to some extent on the cooling capacity available because the reaction is exothermic. Good results can usually be attained by adding the o-alkylphenol containing the polybasic acid to the stirred concentrated sulfuric acid over a period of about 0.25-8 hours followed by a post-addition stirring period of about 0.25-4 hours.

The benefits of the improved sulfonation process are most apparent when the o-alkylphenol is impure. The impurities present are believed to be oxidation products although knowledge of the chemical identity of the impurities is not crucial to the successful use of the process. Impure o-alkylphenol is readily recognized by its yellow to amber color even though it might assay as high as 99 weight percent o-alkylphenol. For the purpose of the process, "pure" o-alkylphenol is colorless whereas "impure" o-alkylphenol is not colorless and is a yellow to amber shade.

The most apparent advantage of the improved sulfonation process is the increase in the mole ratio of disulfonated product to monosulfonated product. With impure o-sec-butylphenol, following the prior art sulfonation procedure, the mole ratio is usually about 2-2.6:1.0. By following the improved process, this ratio is increased to about 2.7-3.5:1 and generally in the range of 2.8-3.4:1. To obtain this ratio without the use of the polybasic acid would require the use of a purified o-sec-butylphenol.

The following examples serve to illustrate the new process and the advantage resulting from it.

EXAMPLE 1-4

This example is for comparative purposes and shows the sulfonation results obtained with impure amber o-sec-butylphenol without the use of polybasic acid.

In a reaction vessel was placed 108 ml. con. (97 weight percent) sulfuric acid. This was stirred and heated to 50° C. Then 98 ml. of impure amber o-sec-butylphenol was added drop-wise over a 10 minute period at 50°-95° C. This mixture was then stirred for two hours at 95° C. and then analyzed by NMR to measure the mole ratio of disulfonated o-sec-butylphenol to monosulfonated o-sec-butylphenol.

The above procedure was repeated four times with the results shown in Table I.

TABLE I

| Example | Di-/Mono-sulfonate Mole Ratio |
|---------|-------------------------------|
| 1 | 2.26 |
| 2 | 2.5 |
| 3 | 2.09 |
| 4 | 2.49 |
| | Average 2.3 |

The procedure used in Example 1-4 was then repeated three times using the same amber o-sec-butylphenol, but this time adding an IPA solution of oxalic acid to the impure o-sec-butylphenol in an amount to provide 0.01 weight percent oxalic acid. The results following this improved procedure are given in Table II.

TABLE II

| Example | Di-/Mono-sulfonate Mole Ratio |
|---------|-------------------------------|
| 5 | 3.00 |
| 6 | 3.10 |
| 7 | 2.82 |
| | Average 3.0 |

From these results it can be seen that by merely adding a small amount of a polybasic carboxylic acid to the reaction, the ratio of di- to mono-sulfonation is substantially increased.

A further embodiment of the invention comprises subjecting the high disulfonic acid o-alkylphenol product to a nitration step to yield dinitro-o-alkylphenol of high purity being substantially free of insoluble tar. This is readily accomplished by mixing the sulfonated o-alkylphenol with a nitrating agent. The nitrating agent is nitric acid or a salt of nitric acid.

The nitric acid concentration is not critical. The concentration can range from about 10-70 weight percent $HNO_3$. A more preferable concentration range is about 15-50 weight percent $HNO_3$. Best results with sulfonated o-sec-butylphenol have been achieved using a nitric acid concentration of about 20 weight percent.

The amount of nitric acid should be an amount which provides at least 2 moles of nitric acid per mole of original o-alkylphenol because the product target is dinitro-o-alkylphenol. A useful range is about 2-5 moles of nitric acid per mole of original o-alkylphenol and more preferably about 2.5-3.5 moles of nitric acid per mole of original alkylphenol.

The nitration temperature can vary over a wide range. A useful range is about 20° C. up to reflux. A more preferred range is about 35°-100° C. Usually the reaction is started by feeding the sulfonated o-alkylphenol to the nitric acid at about 35°-65° C. and then allowing the heat of the reaction to increase the temperature to about 90°-100° C. After completion of the addition, the mixture is preferably stirred at elevated temperatures (approximately 90°-100° C.) for a period sufficient to complete the nitration (approximately 1-4 hours).

Following the nitration, the reaction mixture is allowed to separate and the acid layer is subjected to proper disposal methods. The organic layer may be water washed and dried. Washing is not required and a useful product can be obtained by merely blowing air or more gas through the liquid at elevated temperature (e.g. 100° C.) to drive off water.

Alternatively, a nitric acid salt can be used as the nitrating agent. Preferred salts are the alkali metal salts such as sodium or potassium nitrate. These are used in the form of aqueous solutions. The amount of nitrate salt should provide at least 2 moles of nitrate anion per mole of original o-alkylphenol and more preferably about 2.5-3.5 moles per mole of original alkylphenol. The amount of water used to make the solution can vary over a wide range. Preferably, the nitrate salts concentration should be about 20-60 weight percent and more preferably about 30-50 weight percent.

The nitration is conducted in the same manner as with nitric acid by adding the crude sulfonated o-alkylphenol to the aqueous nitrate salt. Addition can start at about 35°-65° C. and a temperature allowed to increase to about 90°–100° C. A post-addition reaction time of about 1–4 hours at 90°–100° C. is beneficial.

Product is recovered in the same manner as when using nitric acid by allowing the water phase to separate and removing it. The organic phase can be water washed but this is not critical. The organic phase can be dried by heating while passing air or an inert gas through it or by applying vacuum.

The following examples illustrate the second stage of the overall process.

EXAMPLE 8

In a reaction vessel was placed 335 ml. of 20 weight percent nitric acid. This was stirred and warmed to 50° C. and then the sulfonate mixture made as in Example 5 was added drop-wise while the temperature was controlled below 100° C. The mixture was then stirred at 100° C. for 2 hours. Stirring was stopped and the aqueous phase separated and was removed at 95° C. A second separation was conducted at 38° C. and additional aqueous phase was removed. The product was dried by heating at 100°–105° C. while bubbling air through the product. No tar was found in the product which was mainly 2,4-dinitro-6-sec-butylphenol.

EXAMPLE 9

In a reaction vessel place 81 grams of water and 54 grams of sodium nitrate. Stir and heat to 95° C. and then slowly add the sulfonated o-sec-butylphenol made as in Example 6. Maintain temperature at 95°–98° C. during the addition. After the addition, stir at 95–98° C. for one hour. Stop stirring and allow the phases to separate. Drain the water phase and then wash the organic phase with about 85 ml. of water and again remove the water phase which is now the upper phase. Dry the product by heating at 100° C. and 10–50 mm. Hg. The product is mainly 2,4-dinitro-6-sec-butylphenol which is free of any tar residue.

We claim:

1. In a process for sulfonating an impure o-alkylphenol to form a disulfonated o-alkylphenol, said process comprising reacting an impure o-alkylphenol with concentrated sulfuric acid, the improvement comprising adding about 0.001–0.5 weight percent of an aliphatic polybasic carboxylic acid having 2–12 carbon atoms or salt thereof to said o-alkylphenol whereby the ratio of disulfonated to monosulfonated o-alkylphenol is increased.

2. A process of claim 1 wherein said polybasic carboxylic acid is selected from the group consisting of oxalic acid, citric acid, and tartaric acid and mixtures thereof.

3. A process of claim 2 wherein said o-alkylphenol is o-sec-butylphenol.

4. A process of claim 3 wherein said polybasic carboxylic acid is oxalic acid.

5. A process of claim 4 wherein the amount of said oxalic acid added is about 0.005–0.02 weight percent.

6. A process of claim 2 wherein said polybasic carboxylic acid is oxalic acid.

7. A process for making 2,4-dinitro-6-alkylphenol, said process comprising
   (a) mixing about 0.001–0.5 weight percent of an aliphatic polybasic carboxylic acid or salt thereof with an impure o-alkylphenol,
   (b) reacting said impure o-alkylphenol containing said polybasic carboxylic acid or salt with concentrated sulfuric acid in an amount of at least 2.0 moles of sulfuric acid per mole of said o-alkylphenol at a temperature of about 30°–150° C. to form sulfonated o-alkylphenol,
   (c) reacting said sulfonated o-alkylphenol with a nitrating agent selected from the group consisting of nitric acid and salts thereof in an amount of at least 2.0 moles of nitrating agent per mole of said o-alkylphenol at a temperature of about 30°–150° C., and
   (d) recovering a dinitro-o-alkylphenol product of high purity being substantially free of insoluble tar.

8. A process of claim 7 wherein said polybasic carboxyic acid is selected from the group consisting of oxalic acid, citric acid, tartaric acid and mixtures thereof and salts thereof.

9. A process of claim 8 wherein said o-alkylphenol is o-sec-butylphenol.

10. A process of claim 8 wherein said polybasic carboxylic acid is oxalic acid or salts thereof.

11. A process of claim 10 wherein said o-alkylphenol is o-sec-butylphenol.

* * * * *